United States Patent [19]

Meneghin

[11] Patent Number: 4,748,271

[45] Date of Patent: May 31, 1988

[54] PROCESS FOR THE PREPARATION OF CIS-5-FLUORO-2-METHYL-1-(4-METHYL-THIOBENZYLIDENE)-INDENE-3-ACETIC ACID

[75] Inventor: Mariano Meneghin, Treviso, Italy

[73] Assignee: Zambon S.p.A., Milan, Italy

[21] Appl. No.: 875,405

[22] Filed: Jun. 17, 1986

[30] Foreign Application Priority Data

Jun. 19, 1985 [IT] Italy ................. 21215 A/85

[51] Int. Cl.$^4$ ................. C07C 147/107; C07C 147/11
[52] U.S. Cl. ................. 562/428; 562/429
[58] Field of Search ................. 562/428

[56] References Cited

U.S. PATENT DOCUMENTS

| | | | |
|---|---|---|---|
| 3,692,651 | 9/1972 | Sletzinger | 562/428 |
| 3,766,259 | 10/1973 | Sletzinger et al. | 562/428 |
| 3,932,498 | 1/1976 | Shen et al. | 562/428 |

OTHER PUBLICATIONS

Shuman et al., Journal of Organic Chemistry, vol. 42, No. 11, 1977, pp. 1914–1919.

Primary Examiner—Donald B. Moyer
Assistant Examiner—Patricia M. Scott
Attorney, Agent, or Firm—Stevens, Davis, Miller & Mosher

[57] ABSTRACT

A process is described for the preparation of cis-5-fluoro-2-methyl-1-(4-methylthiobenzylidene)-indene-3-acetic acid that consists in reacting a lower alkyl ester of 5-fluoro-2-methylindene-3-acetic acid with a substantially equimolecular amount of 4-methylthio-benzaldehyde in a solid-liquid two-phase system in which the solid phase is a potassium alcoholate or hydroxide and the liquid phase is a solution of the reagents in an organic solvent inert in the reaction conditions, in the presence of a phase transfer catalyst and at a temperature comprised between −20° and +20° C.

9 Claims, No Drawings

PROCESS FOR THE PREPARATION OF CIS-5-FLUORO-2-METHYL-1-(4-METHYL-THIOBENZYLIDENE)-INDENE-3-ACETIC ACID

The present invention relates to a process for the preparation of cis-5-fluoro-2-methyl-1-(4-methylthiobenzylidene)-indene-3-acetic acid and more particularly relates to a process to obtain the above acid with a very low content of trans isomer.

5-fluoro-2-methyl-1-(4-methylthiobenzylidene)-indene-3-acetic acid provides by oxidation the corresponding 1-(4-methylsulfinyl)benzylidene derivative of which the cis isomer is an important compound with anti-inflammatory activity known with the common name of Sulindac and described in U.S. Pat. No. 3,654,349.

In this Patent as well as in other later Patents different syntheses of Sulindac and intermediates thereof have been described. One of the most widely used processes described in the above U.S. Patent comprises, in the last steps, the condensation of 5-fluoro-2-methyl-indene-3-acetic acid (II) or an ester thereof with 4-methylthiobenzaldehyde (III) in the presence of a strong base in an organic solvent. So 5-fluoro-2-methyl-1-(4-methylthiobenzylidene)-indene-3-acetic acid (I) or an ester thereof is obtained by which Sulindac is prepared by an eventual hydrolysis and by oxidation of the methylthio group.

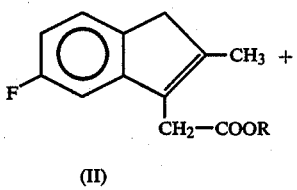

(II)

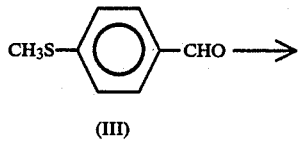

(III)

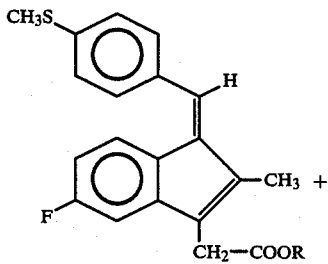

(I-cis)

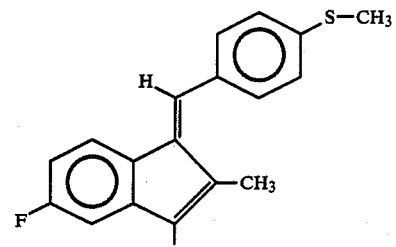

(I-trans)

[R=H, lower alkyl].

The reaction is carried out, according to what is described in U.S. Pat. No. 3,654,349, in methanol, under nitrogen, at the reflux temperature and in the presence of sodium methoxide as a strong base.

The product of the reaction, by working according to what is described in the above Patent, consists of a mixture of cis and trans isomers in which the trans isomer is about 10–12% (see example 4).

A product employed for pharmaceutical use must satisfy severe purity requirements. since Sulindac, as approved as a drug, consists of the cis isomer, it is necessary that the final product does not contain the trans isomer or contains it at most in amounts not higher than 1%. In fact, according to Pharmacopoeial requirements, Sulindac must have a purity of 99% at least.

Therefore it is necessary to purify the product from the trans isomer.

This may be realized, at intermediate level or end product, by successive crystallizations with a remarkable loss of cis isomer. This inconvenience is felt very much as shows the fact that processes were patented for cis-trans isomerization at the level of oxidized product by treatment with iodine in benzene at reflux or by irradiation with ultra-violet light (U.S. Pat. No. 3,692,651) with the evident purpose to recover, at least partially, the product which otherwise would be lost.

We have now unexpctedly found that, if the condensation between the compound II in the form of an ester and the compound III is carried out in a liquid two-phase system in which the solid phase consists of a potassium alcoholate or hydroxide and the liquid phase consists of an inert organic solvent and in the presence of a phase transfer catalyst, the product (I-cis) is obtained with high yields in the form of free acid, containing very low amounts (lower than 3% and often than 1%) of the corresponding trans isomer.

Therefore, object of the present invention is a process for the preparation of cis-5-fluoro-2-methyl-1-(4-methylthiobenzylidene)indene-3-acetic acid (I-cis, R=H) consisting in condensing in a two-phase system, under the above reported conditions, a lower alkyl ester of 5-fluoro-2-methyl-indene-3-acetic acid (II, R=lower alkyl) with 4-methylthiobenzaldehyde (III).

For clearness, the characterizing features and parameters of the process object of the invention are here below reported in a schematic way:

a—Starting products: 4-methylthiobenzaldehyde (III) and lower alkyl ester of 5-fluoro-2-methyl-indene-3-acetic acid (II, R=lower alkyl). Methyl ester (II, R=CH$_3$) is preferably used.

b—Solid phase: subdivided solid potassium alcoholate or hydroxide. Potassium hydroxide in scales is preferably used.

c—Liquid phase: a solution of the reagents in an organic solvent inert in the reaction conditions. Suitable solvents are aromatic hydrocarbon solvents. Ethylbenzene, toluene, benzene or chlorobenzene are preferably used.

d—Phase transfer catalysts: in general tetraalkylammonium salts, tetraalkylphosphonium salts and crown ethers are suitable as phase transfer catalysts. It was observed that hydroxides and bisulfates of tetraalkylammonium do not provide the desired selectivity and then are not suitable for the purposes of the present invention.

In practice the preferred catalysts are those having a lipophilic character, for instance ammonium or phosphonium salts containing long chain alkyl radicals or those having a total number of carbon atoms higher than 12. For economic reasons, tetraalkylammonium or tetraalkylphosphonium halides are preferred. From the economic point of view as well as from the point of view of the results tricaprylyl-methyl-ammonium chloride is particularly preferred.

e—Molar ratio between the reagents: it is substantially equimolecular optionally with a slight excess (5-10%) of aldehyde (III).

f—Molar ratio between base and compound II: potassium alcoholate or hydroxide is used in a molar ratio comprised between 2:1 and 3:1 with respect to the ester of formula II.

g—Amount of phase transfer catalyst: it is not critical within the usual ranges. Generally the catalyst is used in amounts comprised between 2 and 10% (w/w) with respect to the ester of formula II, preferably between 5 and 10%.

h—Concentration of the reagents in the liquid phase: it is not critical within the usual ranges. For industrial economic reasons relatively concentrated solution (10-15% w/w) are preferred.

i—Reaction temperature: the reaction is carried out between −20° and +20° C., preferably between −15° and +15° C. for practical reasons.

The process object of the invention comprises, then, two stages (condensation and hydrolysis) which take place contemporaneously in the same reaction environment. The condensation reaction seems to be more fast. For this reason at first it is observed an accumulation of the compound I in the form of an ester (I, R=lower alkyl) but at the end of the reaction, after the acid-base separation, the free acid (I, R=H) is the only product.

In a practical embodiment, the process object of the invention is performed by preparing a solution of the ester II in the organic solvent and by suspending potassium alcoholate or hydroxide.

The suspension assumes a violet colour and is kept under stirring for 2 hours at least.

Then a solution of the phase transfer catalyst in the same solvent and successively, in about 1-2 hours, a solution of 4-methylthiobenzaldehyde, always in the same organic solvent, are added.

The course of the reaction is followed by traditional analytical methods, for instance by following the disappearance of the ester II by thin layer chromatography (TLC).

After about 1-2 hours the condensation is finished and after other 2-3 hours the hydrolysis reaction is finished too.

The reaction mixture is worked according to conventional techniques to isolate the free acid (I, R=H). During the whole course of the reactions the reaction mixture is kept under stirring at the selected temperature within the above reported values. In consideration of the different reaction rates between the condensation and the hydrolysis, it is possible to begin the reaction at lower temperatures (for instance −15° C.) and to raise the temperature (for instance at +15° C.) when, following the course of the reaction, it is observed that the ester of formula II has practically disappeared. This way of proceeding has the aim to complete the hydrolysis reaction in a short time. The process of the invention provides the acid of formula I-cis with yields higher than 90% and with a content of trans isomer lower than 3%. The content of trans isomer, by working within the preferred limits of the above reported parameters, is often lower than 0.2%. So low contents of trans isomer do not require any specific separation.

The normal operations of purification in the subsequent steps of the synthesis of Sulindac eliminate the small percentage of trans isomer that is eventually present.

In order to better illustrate the invention without limiting it yet, the following examples are now given.

EXAMPLE 1

To a solution of methyl 5-fluoro-2-methyl-indene-3-acetate (5 g; 0.0227 mol) in toluene (100 ml) kept under stirring under nitrogen at the temperature of 15° C., potassium hydroxide in powder (3.71 g; 0.066 mol) is added.

After three hours under stirring in the same conditions, a solution of tricaprylyl-methyl-ammonium chloride (0.5 g; 0.0012 mol) in toluene (2 ml) and then, dropwise, a solution of 4-methylthiobenzaldehyde (4g; 0.026 mol) in toluene (4 ml) are added to the mixture.

The mixture is kept under the same conditions for other twelve hours, then 150 ml of demineralized water are added and it is heated at 40° C. for 30 minutes.

Two layers are formed. The aqueous phase is separated and added slowly to a solution of hydrochloric acid at 33% (10 g) in water (40 g) at a temperature of 15° C.

After further 30 minutes under stirring the precipitate, which is formed, is collected by filtration, washed with demineralized water and dried in a drying stove in vacuum at 70° C.

5-fluoro-2-methyl-1-(4-methylthiobenzylidene)-indene-3-acetic acid is obtained (92% yield).

The product is analyzed by high pressure liquid chromatography (HPLC) as follows:

Solvent A: phosphate buffer ($NH_4H_2PO_4$) 0.05M at pH=3.

Solvent B: methanol at pH=3.

Chromatographic conditions:

Liquid chromatograph HPL mod. 1084/B, with an U.V. detector with unsettled wave length and automatic injector.

Column Brawlee RP8 (5 mcm) 250×4.6 cm 8D.
Flow: 1.70 ml/min.
Solvent B: 60%.
Solvent A temperature: 60° C.
Solvent B temperature: 40° C.
Column temperature: 45° C.
Wave length: 268 nm.
Sample concentration 1 mg/ml in methanol.

The HPLC analysis shows that the product consists of the cis isomer of the desired acid ($R_t = 14.39$ minutes) while the corresponding trans isomer ($R_t = 12.99$ minutes) is present in traces (equal to or lower than 0.15%).

EXAMPLE 2

To a solution of methyl 5-fluoro-2-methyl-indene-3-acetate (50 g; 0.227 mol) in toluene (700 ml) kept under stirring, under nitrogen at 15° C., potassium hydroxide in scales (36.21 g; 0.647 mol) is added.

The mixture is kept under stirring in the same conditions for three hours, then it is cooled at −15° C. and a solution of tricaprylyl-methyl-ammonium chloride (4.88 g; 0.0121 mol) in toluene (20 ml) is added. Then, always under stirring and under nitrogen at −15° C., a solution of 4-methylthiobenzaldehyde (39 g; 0.265 mol) in toluene (39 ml) is added dropwise in 2 hours.

The course of the reaction is followed by thin layer analysis (TLC). After 4 hours the starting product has practically disappeared and the main product is the methyl ester of 5-fluoro-2-methyl-1-(4-methylthiobenzylidene)-indene-3-acetic acid.

The temperature of the reaction mixture is raisen at 15° C.

The stirring under nitrogen is continued and the course of the reaction is monitored by TLC.

After 3 hours the hydrolysis of the ester is complete.

468 ml of demineralized water are added and, after 30 minutes, the mixture is heated at 40° C.

Two layers are formed. The aqueous phase is separated and added dropwise to a solution of 157 g of hydrochloric acid at 16.5%.

The precipitate is separated by filtration, washed with demineralized water and dried in a drying stove in vacuum at 60° C. 5-fluoro-2-methyl-1-(4-methylthiobenzylidene)-indene-3-acetic acid is obtained (yield 93%).

The HPLC analysis performed according to the conditions reported in example 1, shows that the compound consists of the cis isomer, the trans isomer being present in amounts equal to lower or than 0.15%.

EXAMPLE 3

By working according to the procedure described in example 1 the experiments reported in the following table were carried out.

TABLE

Preparation of compound I-cis according to the operative modalities of example 1.

| Solvent | Solid phase | PTC[1] | I-trans isomer[2] |
|---|---|---|---|
| Chlorobenzene | KOH[3] | TCMAC | 0.38% |
| Ethylbenzene | KOH | TCMAC | 1.57% |
| Benzene | KOH | TCMAC | 0.24% |
| Toluene | KOH | TCMAC | Traces[4] |
| Toluene | CH$_3$OK | TCMAC | 1.62% |
| Toluene | t.C$_4$H$_9$OK | TCMAC | 2.95% |
| Toluene | KOH | TBAB | 1.06% |
| Toluene | KOH | TBA I | 2.65% |
| Toluene | KOH | TBPC | 1.76% |
| Toluene | KOH | TEAB | 2.19% |
| Toluene | KOH | TPAB | 1.60% |
| Toluene | KOH | TESAC | 2.68% |
| Toluene | KOH | TESAB | 0.16% |
| Toluene | KOH | TESA I | 1.76% |
| Toluene | KOH | TMEAB | 0.23% |
| Toluene | KOH | TBEPB | 0.79% |
| Toluene | KOH | DB-18-6 | 1.65% |
| Toluene | KOH | DC-18-6 | 1.92% |

Notes to the Table
[1]PTC = phase transfer catalyst
TCMAC = tricaprylyl-methyl-ammonium chloride
TBAB = tetrabutyl-ammonium bromide
TBAI = tetrabutyl-ammonium iodide
TBPC = tetrabutyl-phosphonium chloride
TEAB = tetrapropyl-ammonium bromide
TPAB = tetrapropyl-ammonium bromide
TESAC = tetrahexyl-ammonium chloride
TESAB = tetrahexyl-ammonium bromide
TESAI = tetrahexyl-ammonium iodide
TMEAB = trimethyl-hexadecyl-ammonium bromide
TBEPB = tributyl-hexadecyl-phosphonium bromide
DB-18-6 = dibenzo-18-crown-6
DC-18-6 = dicyclohexyl-18-crown-6
[2]The percentage of I-trans isomer was determinated by HPLC according to the method described in example 1.
[3]Potassium hydroxide in scales was used.
[4]The amount of trans isomer resulted lower than 0.15%. The experiment is described in detail in example 1.

EXAMPLE 4

The present comparison example repeats the method described in example 10 point E of the U.S. Pat. No. 3,654,349.

A solution of 5-fluoro-2-methyl-indene-3-acetic acid (15 g; 0.072 mol), 4-methylthiobenzaldehyde (14 g; 0.091 mol) and sodium methoxide (13 g; 0.24 mol) in methanol (200 mol) is heated under stirring at 60° C. under nitrogen for 6 hours.

After cooling, the reaction mixture is poured into water and ice (750 ml) and acidified with hydrochloric acid 2.5N.

A solid precipitates and is collected by filtration and triturated with a small amount of ethyl ether.

Then the solid is dried in a drying stove in vacuum at 60° C. 25.83 g of 5-fluoro-2-methyl-1-(4-methylthiobenzylidene)-indene-3-acetic acid are obtained and analysed by HPLC according to the method described in example 1.

The HPLC analysis shows that the obtained product has a purity of 91.6% and consists, referring to the amount of 5-fluoro-2-methyl-1-(4-methylthiobenzylidene)-indene-3-acetic acid, of the cis isomer (88.8%) and of the trans isomer (11.2%).

I claim:
1. A process for the preparation of cis-5-fluoro-2-methyl-1-(4-methylthiobenzylidene)-indene-3-acetic acid consisting of reacting a lower alkyl ester of 5-fluoro-2-methyl-indene-3-acetic acid with a substantially equimolecular amount of 4-methylthiobenzaldehyde in a solid-liquid two-phase system in which the solid phase is a potassium alcoholate or hydroxide in a molar ratio comprised between 2:1 and 3:1 with respect to the lower alkyl ester of 5-fluoro-2-methyl-indene-3-acetic acid and the liquid phase is a solution of the reagents in an organic solvent inert under the reaction conditions, in the presence of a phase transfer catalyst which promotes the selective formation of the cis-isomer and at a temperature comprised between −20° and +20° C.

2. A process according to claim 1 in which the lower alkyl ester of 5-fluoro-2-methyl-indene-3-acetic acid is the methyl ester.

3. A process according to claim 1 in which the phase transfer catalyst is a tetraalkyl-ammonium or tetraalkyl-phosphonium halide.

4. A process according to claim 1 in which the phase transfer catalyst is tricaprylyl-methyl-ammonium chloride.

5. A process according to claim 1 in which the inert organic solvent is an aromatic hydrocarbon.

6. A process according to claim 1 in which the inert organic solvent is selected from toluene, benzene, ethylbenzene and chlorobenzene.

7. A process according to claim 1 in which the phase transfer catalyst is used in an amount comprised between 2 and 10% w/w, with respect to the starting ester.

8. A process according to claim 1 in which the temperature is between $-15°$ and $+15°$ C.

9. A process according to claim 1 in which methyl ester of 5-fluoro-2-methyl-indene-3-acetic acid reacts with a substantially equimolecular amount of 4-methylthio-benzaldehyde in a solid-liquid two-phase system in which the solid phase is KOH in scales and the liquid phase is a solution of the reagents in toluene, in the presence of tricaprylyl-methyl-ammonium chloride as phase transfer catalyst and at a temperature between $-15°$ and $15°$ C.

* * * * *